United States Patent
Ng

(10) Patent No.: US 7,793,552 B2
(45) Date of Patent: Sep. 14, 2010

(54) HIGH SUCTION DOUBLE-CELL EXTRACTOR

(75) Inventor: Charles Wang Wai Ng, Kowloon (CN)

(73) Assignee: The Hong Kong University of Science and Technology, Kowloon (HK)

(*) Notice: Subject to any disclaimer, the term of this patent is extended or adjusted under 35 U.S.C. 154(b) by 47 days.

(21) Appl. No.: 12/194,312

(22) Filed: Aug. 19, 2008

(65) Prior Publication Data

US 2009/0049924 A1  Feb. 26, 2009

Related U.S. Application Data

(60) Provisional application No. 60/965,214, filed on Aug. 20, 2007.

(51) Int. Cl.
 *G01N 3/08* (2006.01)
(52) U.S. Cl. .......................................... 73/818; 73/760
(58) Field of Classification Search ................. 73/760, 73/818, 865.6, 865.8, 866
 See application file for complete search history.

(56) References Cited

U.S. PATENT DOCUMENTS

| | | | | |
|---|---|---|---|---|
| 3,673,861 A | * | 7/1972 | Handy | 73/841 |
| 4,715,212 A | * | 12/1987 | Johanson | 73/38 |
| 4,734,649 A | * | 3/1988 | Barnaby | 324/376 |
| 5,044,860 A | * | 9/1991 | Norem et al. | 414/287 |
| 6,546,782 B1 | * | 4/2003 | De La Cruz et al. | 73/7 |
| 6,718,835 B2 | * | 4/2004 | Wang et al. | 73/866 |
| 7,325,444 B2 | * | 2/2008 | Butler | 73/73 |
| 2005/0146708 A1 | * | 7/2005 | Shi et al. | 356/35.5 |

OTHER PUBLICATIONS

Charles W. W. Ng et al., "Influence of Stress State on Soil-Water Characteristics and Slope Stability", Feb. 2000, Journal of Geotechnical and Geoenvironmental Engineering, vol. 126, No. 2, pp. 157-166.

A. W. Bishop et al., "A Hydraulic Triaxial Apparatus for Controlled Stress Path Testing", 1975, Geotechnique 25, No. 4, pp. 657-670.

(Continued)

*Primary Examiner*—Max Noori
(74) *Attorney, Agent, or Firm*—Buchanan Ingersoll & Rooney PC

(57) ABSTRACT

A high suction double-cell extractor includes an outer cell defining an outer chamber, and an open-ended inner cell defining an inner chamber. The inner chamber is bottle-shaped and has a neck. The high suction double-cell extractor also includes a vertical loading system for applying axial force on a soil specimen during extraction. The high suction double-cell extractor also includes a port for introduction of pressurized air supply into the outer and inner cells. The introduced pressurized air can apply cell pressure on the soil specimen during extraction. The high suction double-cell extractor also includes a relative humidity control system and a differential pressure detector system. The high suction double-cell extractor can be used to measure stress-dependent soil-water characteristics curve (SDSWCC) under various stress states three-dimensionally and more accurately, and under total suction up to 8,000 kPa.

23 Claims, 3 Drawing Sheets

OTHER PUBLICATIONS

C. F. Chiu et al., "A State-Dependent Elasto-Plastic Model for Saturated and Unsaturated Soils", 2003, Geotechnique 53, No. 9, pp. 809-829.

C. W. W. Ng et al., "A New Simple System for Measuring Volume changes in Unsaturated Soils", 2002, Can. Geotech. J. 39, pp. 757-764.

D. G. Fredlund, Ph.D. et al., "Measurements of Soil Suction", *Soil Mechanics for Unsaturated Soils,* Chapter 4, John Wiley & Sons, Inc., 1993, p. 64.

Soil-Water Characteristics Cell, GCTS Testing Systems, 2005, p. 17.

* cited by examiner

HIGH SUCTION DOUBLE-CELL EXTRACTOR

CROSS-REFERENCE TO RELATED APPLICATIONS

This application claims priority to U.S. Provisional Patent Application 60/965,214, filed on 20 Aug. 2007, the entirety of which is incorporated by reference herein.

FIELD OF THE INVENTION

This disclosure concerns an invention relating generally to pressure plate extractor for measurements of stress-dependent soil-water characteristic curve (SDSWCC), more specifically to High Suction Double-Cell Extractor, and even more specifically to Stress Controllable High Suction Double-cell Volumetric Pressure Plate Extractor.

BACKGROUND OF THE INVENTION

Almost all soil slopes on land are initially unsaturated in nature. In order to determine the factor of safety of unsaturated slopes accurately, it is essential to calculate transient seepage and hence pore water pressures in the soil. To do so, one has to measure the so-called soil-water characteristic curve (SWCC), which defines the relationship between the soil suction and either the water content or the degree of saturation of the soil. Conventionally SWCC of a soil is measured by means of a pressure plate extractor in which no confining stress can be applied and volume change of the soil specimen is assumed to be zero, although it is recognized that the stress state of a soil will affect SWCC theoretically and volume change of the soil specimen will take place when there is a change of soil suction and stress. The Applicant developed and published a one-dimensional volumetric pressure plate extractor in which the total net normal stress can be controlled one-dimensionally and the axial deformation of the soil specimen is measured. The measured stress-dependent SWCC is now called SDSWCC [Ng, C. W. W. and Pang, Y. W. (2000). Influence of stress state on soil-water characteristics and slope stability. *Journal of Geotechnical and Geoenvironmental Engineering*, ASCE. Vol. 126, No. 2. 157-166.].

Since the fundamental concepts behind the Applicant's previous design of the one-dimensional stress controllable pressure plate extractor and the "Fredlund cell" (a product from GCTS Company, model SWC-150, Fredlund SWCC Device) are identical, both of these two devices are suffered from not being able to control stress-state in three-dimensional manner to simulate actual field conditions more closely and correctly. An axis-translation technique is employed in both of these two devices. Hence, the suction is matric suction instead of total suction. Secondly, volume changes of soil specimen cannot be measured accurately because a gap can form between the soil specimen and an oedometer ring at high suctions which cannot be accounted for by measuring vertical displacement of the soil specimen only. Thirdly, the range of suctions that can be applied is limited by the air-entry value of the ceramic disk used (i.e., typically less than 500 kPa). Therefore, any measured SWCC may not be very relevant to some actual field stress conditions and is not accurate. Also since any measured SWCC is limited to a suction range of less than 500 kPa, this will reduce the applicability of the SWCC in engineering problems and soil types severely.

To improve the accuracy of volume change measurement, a new "total volume change measuring system" is developed and published by the Applicant and his colleagues [Ng, C. W. W., Zhan, L. T. and Cui, Y. J. (2002). A new simple system for measuring volume changes in unsaturated soils. *Canadian Geotechnical Journal*. Vol. 39, No. 3, 757-764]. In the 2002 design of total volume measuring system, the volume change of the soil specimen during extraction is measured by measurement of difference of water level in a reference tube and in the inner cell, in particular at the neck of the inner cell.

Based on current widely accepted theoretical framework, unsaturated soil behavior and properties are recognized to be governed by at least two stress-state variables, i.e. net normal stress and metric suction. At present, no simple and accurate experimental system is available to measure soil-water characteristic curves under various three-dimensional stress states and high total suctions, up to 8,000 kPa.

This significance of this new invention is to overcome the above shortcomings by controlling stress state of a soil specimen three-dimensionally, by measuring the actual total volume changes of the soil specimen accurately, and by making use of relative humidity (RH) to control total suction up to 8,000 kPa.

SUMMARY OF THE INVENTION

To give the reader a basic understanding of some of the advantageous features of the invention, following is a brief summary of preferred versions of the invention. As this is merely a summary, it should be understood that more details regarding the preferred versions may be found in the Detailed Description set forth elsewhere in this document. The claims set forth at the end of this document then define the various versions of the invention in which exclusive rights are secured.

A preferred version of a pressure plate extractor constructed in accordance with the invention mainly includes three parts, namely, a double-cell extraction device, a differential pressure detector system and a relative humidity (RH) control system.

First of all, the pressure plate extractor has a double-cell extraction device. The outer cell of the extraction device comprises of a top plate, a cylindrical sidewall and a base plate. Therefore, an outer chamber is defined with the top plate, the sidewall and the base plate.

The extraction device has an inner cell which is mounted within the outer cell. The inner cell is open-ended, and is mounted onto the base plate sealed with rubber sealing O-rings. Therefore, an inner chamber is defined within the inner cell.

Preferably, a supporting means can be provided in the outer cell for supporting the inner cell and a soil specimen to be tested.

The inner cell is open to the outer cell through an opening at the upper portion of the inner cell. The opening at the upper portion of the inner cell ensures that an identical pressure can be applied to both the inner and outer cells, hence eliminating any expansion and/or compression of the inner cell caused by pressure differences between the inner and outer cells.

The soil specimen to be tested is placed inside the inner cell. It is important that the soil specimen is wrapped with a membrane during a test. The membrane is water impermeable and resilient. Therefore, accurate measurement of volume change can be obtained without any gap formed between the soil specimen and its container, as compared with that in previous designs.

The inner chamber is bottle-shaped and has a neck. The change of water level inside the inner cell will be magnified, because the diameter at the neck of the inner cell is smaller than that at the other body of the inner cell. During a test, a change of water level takes place only within the bottle neck. Thus, the measurement of the water level inside the inner cell due to any volume change of the soil specimen becomes more sensitive because of the small cross-sectional area at the bottle neck.

The double-cell extraction device also has a vertical loading system. The loading system can apply axial load to the soil specimen through an opening on the top plate and the neck of the inner cell. Some sealing O-rings are used between the opening on the tope plate and the loading system for air tightness of the extraction device. The vertical loading system also includes an internal load cell for measuring the axial force applied on the soil specimen.

The double-cell extraction device is configured with a port for introduction of pressurized air into the outer and inner cells. The introduced air applies cell pressure on the soil specimen. Therefore, the soil specimen can be tested three-dimensionally by controlling the axial force provided by the vertical loading system in combination with the cell pressure applied by the pressurized air supply.

In order to measure the water level change inside the inner cell resulted from volume change of soil specimen during extraction, a reference tube is provided inside the outer cell. It is important that the water level in the reference tube remains constant during the test. The reference tube is supported by a vertical stand. Alternatively, the reference tube is mounted onto the external sidewall of the inner cell to eliminate the displacement of the reference tube when the pressurized air is applied inside the outer cell.

Secondly, the pressure plate extractor has a high-accuracy differential pressure detector system. The differential pressure detector is connected with the reference tube and the inner cell to detect any changes of differential pressures between the water level change inside the inner cell due to a volume change of the soil specimen and the constant water level inside the reference tube. A model of "Druck LPM9381" differential pressure transducer is adapted in this invention.

Thirdly, the pressure plate extractor has a relative humidity control system. The control system can control the relative humidity of the soil specimen and hence the total suction by circulating air or water-vapor through the soil specimen during extraction.

Finally, other features are provided for practical operation of the pressure plate extractor. For example, two porous disks are provided for sandwiching the soil specimen and meanwhile allowing air or water-vapor pass through the soil specimen. Additionally, in order to keep the axial force applied on the soil specimen by the vertical loading system maintain uniform, a top cap is provided to cover the porous disks. Furthermore, in order to measure the relative humidity of the soil specimen during extraction, a set of relative humidity sensors is installed at the center portion of the porous disks. Meanwhile, in order to measure the total suction, a set of thermocouple psychrometers is also installed at the center portion of the porous disks.

Advantageously, a pressure plate extractor according to this present invention is suitable for measurement of the stress-dependent soil-water characteristic curve (SDSWCC) by controlling stress states of a soil specimen three-dimensionally, by measuring the actual total volume change of the soil specimen accurately, and by making use of relative humidity control system to control total suction up to 8,000 kPa.

A schematic diagram of the setup is illustrated in FIG. 1. The High Suction Double-cell Extractor comprising:

An outer cell;
An outer chamber within the outer cell;
An inner cell is sealed within the outer cell;
An inner chamber within the inner cell;
A reference tube;
A port in the outer cell for introduction of pressurized air;
A pressurized air supply system;
A dial gauge connecting a vertical loading system through an internal load cell;
Two porous disks sandwich a soil specimen;
Each coarse porous disk is installed a relative humidity sensor at its center portion;
Each coarse porous disk is installed a thermocouple psychrometer at its center portion;
A relative humidity control system is connecting with the porous disks which sandwich the soil specimen;
An air pump is installed between the porous disk and the relative humidity control system;
A flow meter is installed between the porous disk and the relative humidity control system;
A differential pressure detector is connecting with the reference tube and the inner cell.

Throughout the assembling of the aforesaid components, the new pressure plate extractor of this invention can achieve the following: net stress control, measurement of total volume changes of soil specimen and total suction control. The operation and configuration of the new extractor is depicted in the Detailed Description part of this document.

This invention is the development of a new but simple Stress Controllable High Suction Double-cell Volumetric Pressure Plate Extractor, which will enable researchers and engineers to measure stress-dependent soil-water characteristic curve (SDSWCC) accurately, under various stress states three-dimensionally and total suctions up to 8,000 kPa. This means that measured SDSWCC will be relevant to field stress conditions for transient seepage analysis of pore water pressure distributions, which are essential for accurate slope stability calculations and geoenvironmental engineering assessments.

Further advantages, features and objects of the invention will be apparent from the following detailed description of the invention in conjunction with the associated drawings.

DETAILED DESCRIPTION OF PREFERRED EMBODIMENTS OF THE INVENTION

Figure 1:
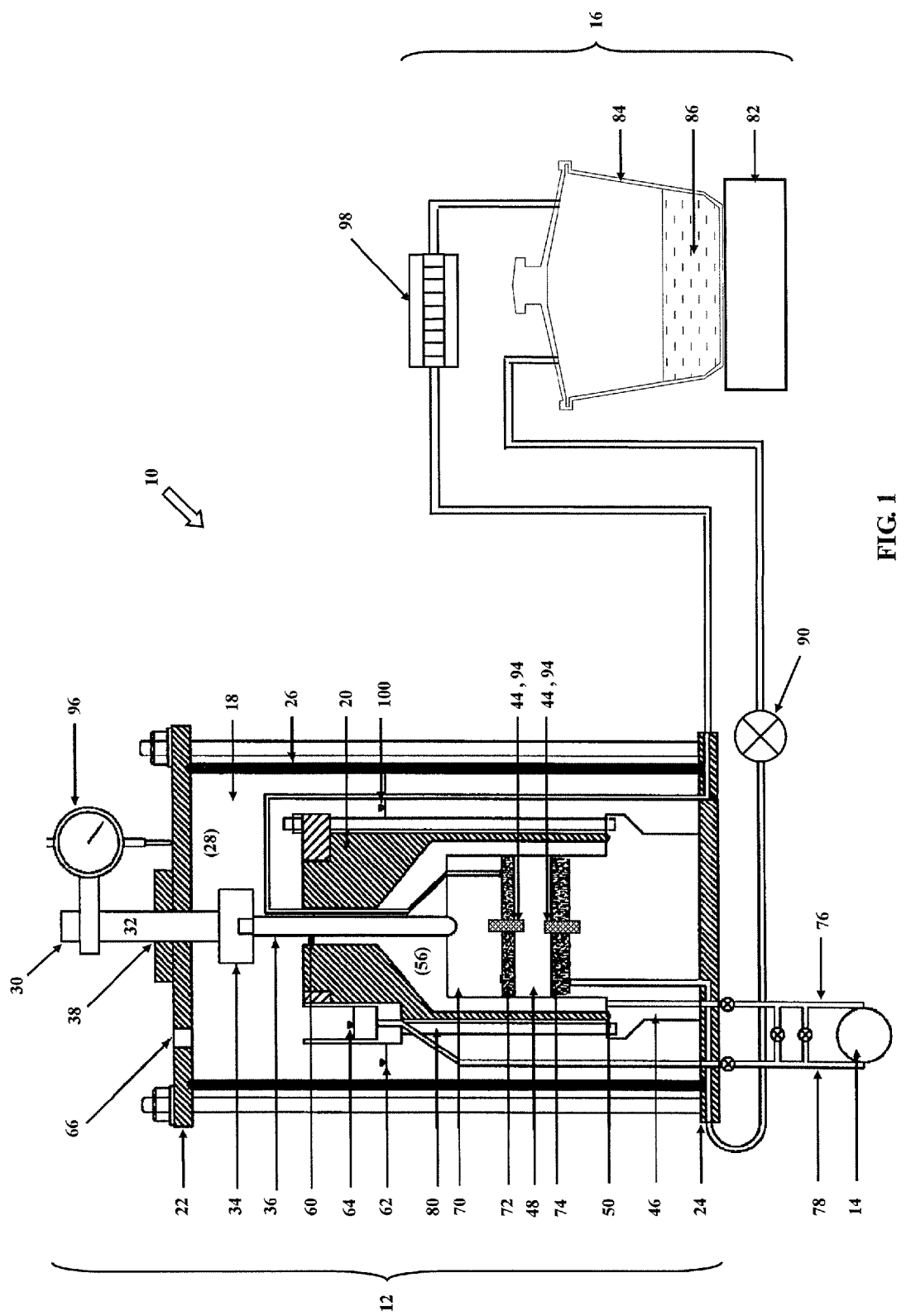
FIG. 1 shows a Schematic Diagram of the Stress Controllable High Suction Double-cell Volumetric Pressure Plate Extractor.
Figure 2:
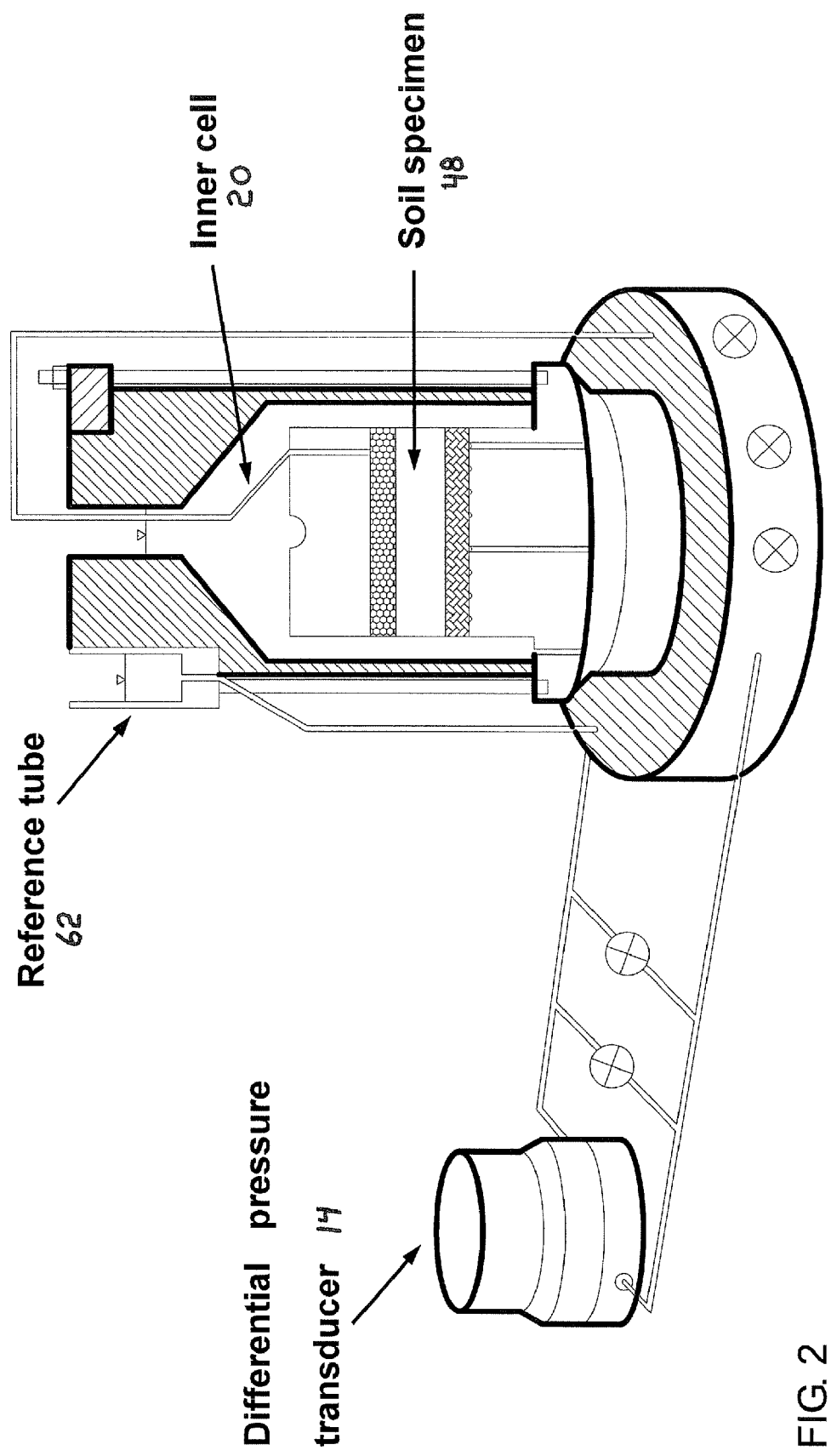
FIG. 2 shows a photograph of the Double-cell Total Volume Measuring Device.
Figure 3:
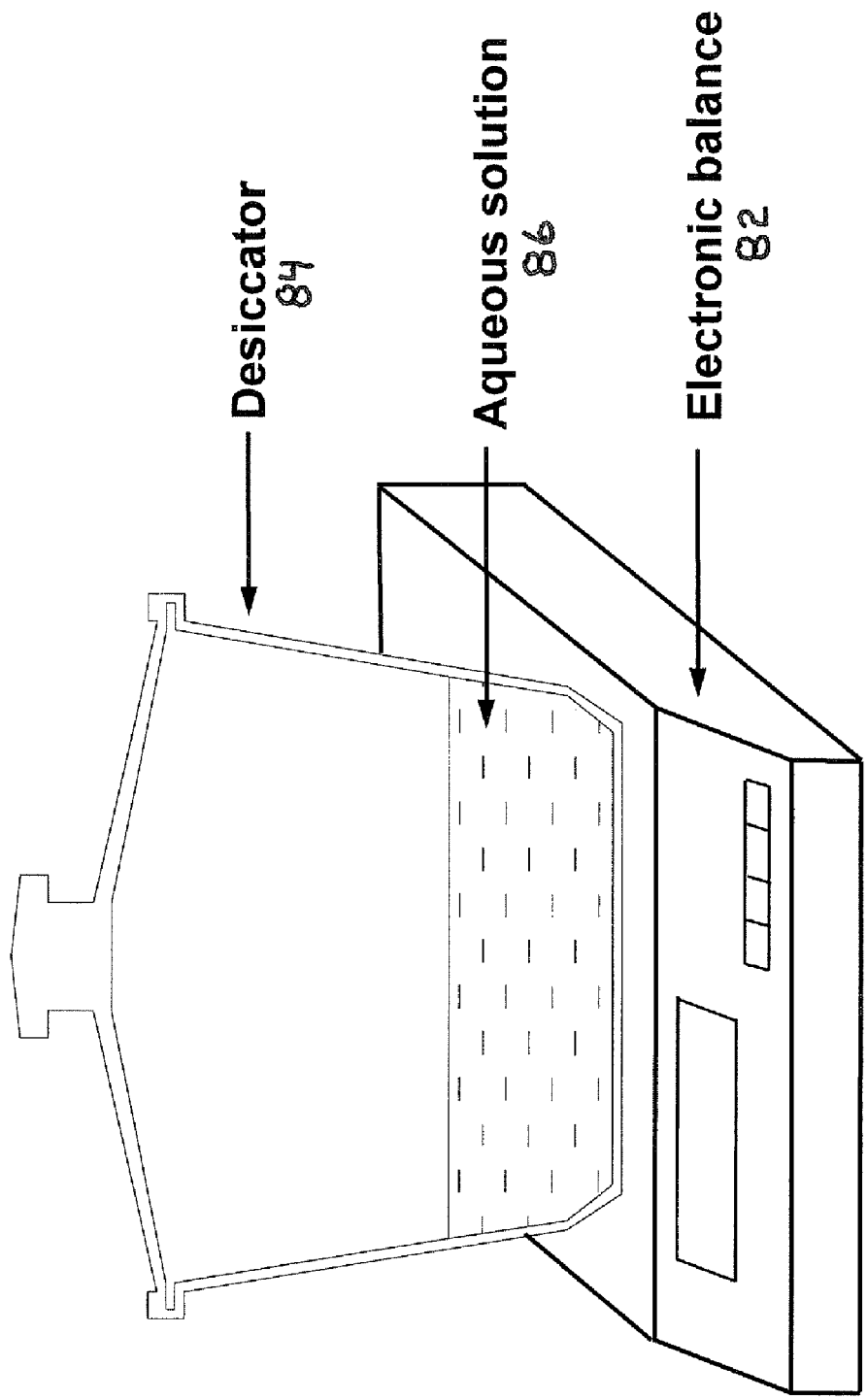
FIG. 3 shows a photograph of the relative humidity control system.

Referring to drawings, an exemplary version of a pressure plate extractor which implements features of the invention is designated generally by the reference numeral 10. The pressure plate extractor 10 includes three main parts, namely a double-cell extraction device 12, a differential pressure detector 14 and a relative humidity control system 16.

The double-cell extraction device 12 includes an outer cell 18 and an inner cell 20. The top plate 22, the base plate 24 and the sidewall 26 are combined together to form the outer cell 18. Therefore, an outer chamber 28 is defined within the outer cell 18. The sidewall 26 has a generally cylindrical configuration and also preferably is transparent to provide a see-through feature. The three parts of the outer cell 18, i.e. the top plate 22, the base plate 24 and the sidewall 26 are held together by bolts and nuts. It is understood that other fixation means could be used to hold the outer cell 18 together and assemble it.

The cylindrical sidewall 26 is sealed to the top plate 22 and to the base plate 24 when assembled by rubber sealing O-rings which are fitted at the both ends of the cylindrical sidewall 26. In order to enhance the sealing effect, preferably the top plate 22 and the base plate 24 respectively includes a depression which can receive the sidewall 26. Alternatively, the sidewall 26 and the base plate 24 could be in an integrated configuration. The top plate 22 and base plate 24 are preferably formed of stainless steel or enhanced aluminum material owing to strengthens, cost and corrosion resistance, though numerous other materials could be used.

There is an opening 38 at the center portion of the top plate 22 to accommodate a vertical loading system 30 to penetrate through the top plate 22. The vertical loading system 30 includes a frictionless loading arm 32, an internal load cell 34 and a loading rod 36. To maintain the air tightness of the outer pressure chamber 28, some rubber sealing O-rings are used between the opening 38 and the loading arm 32. To eliminate any error due to side friction between the frictionless loading arm 32 and the sealing O-rings, an internal load cell 34 is attached between the frictionless loading arm 32 and the loading rod 36 for determining the actual axial force applied on a soil specimen. A dial gauge 96 is mounted on the frictionless loading arm 32 to measure the axial displacement of the soil specimen 48.

There is a port 66 on the top plate 22 for introducing air pressure into the double-cell extraction device 12. The air supply system, which is not shown in the drawings, is a controllable pressurized air source or any air supply means which could supply pressurized air in a controllable way. The introduction of pressurized air into the double-cell extraction device 12 is important for measuring of stress-dependent soil-water characteristic curve (SDSWCC) accurately under various stress states three-dimensionally, because the pressurized air can apply cell pressure on the soil specimen 48 in all directions.

Preferably there is a supporting means 46 on the base plate 24 for supporting the inner cell 20 and the soil specimen 48. A pedestal is used as the supporting means 46 in this invention.

The inner cell 20 is open-ended and preferably has a generally cylindrical bottle-shaped configuration. The lower portion of the inner cell 20 is sealed to the supporting means 46 by rubber sealing O-rings 50 which fitted at the lower portion of the inner cell 20. The inner cell 20 and the supporting means are held together by bolts and nuts. Other alternative sealing means could be used for sealing the inner cell 20 onto the supporting means 46.

Once the inner cell 20 is mounted and sealed onto the supporting means 46, an inner chamber 56 is formed inside the inner cell 20. The upper portion of the inner cell 20 is open to the outer cell 18. The opening of the inner cell 20 ensures that an identical air pressure can be applied to both the inner cell 20 and outer cell 18, hence eliminating any expansion and/or compression of the inner cell 20 caused by pressure differences between the outer cell 18 and the inner cell 20.

A plastic membrane is used for wrapping the soil specimen 48 during a test. The plastic membrane surrounds the soil specimen 48 and covers the two porous disks 72 and 74, sealed by rubber O-rings. The membrane is water impermeable and resilient. So the water in the inner cell 20 will not enter into the soil specimen, and no gap is formed between the soil specimen 48 and the membrane during a test due to the presence of cell pressure.

The inner chamber 56 is bottle-shaped and has a neck, i.e. the diameter of the upper portion of the inner cell 20 is smaller than that at the lower portion of the inner cell 20. During a test, a change of water level 60 takes places only within the bottle neck, i.e. the upper portion of the inner cell 20. Thus, the measurement of the water level change 60 inside the inner cell 20 due to any volume changes of the soil specimen 48 becomes more sensitive because of the small cross-sectional area at the bottle neck.

A reference tube 62 is provided inside the outer cell 18 for comparison with the water level change 60 inside the inner cell 20. The reference tube 62 is supported onto the supporting means 46 by a vertical bar 80. Alternatively the reference tube 62 is mounted onto the external sidewall of the inner cell 20 so that the reference tube 62 could not move relative to the inner cell 20 when the cell pressure is applied during extraction. Furthermore, the diameter of the reference tube 62 is enlarged at the upper portion so that the cross-sectional area of the reference tube 62 is the same as that at the bottle neck of the inner cell 20 during a test, thus the evaporation from the water in the reference tube 62 is identical to that from the inner cell 20. Also the enlarged area can reduce the change of water level 64 in the reference tube 62 resulting from a change of cell pressure.

In order to maintain the axial force applied by the vertical loading system 30 on the soil specimen 48 in a uniform distribution, a top cap 70 is used at the lower end of the loading rod 36. The top cap 70 is made of stainless steel or aluminum. Furthermore, a first porous disk 72 is provided to cover the soil specimen 48 and a second porous disk 74 is provided to support the soil specimen 48 during a test. Hence these two porous disks 72 and 74 can sandwich the soil specimen 48 during extraction, on one hand for further uniformly distributing the force and/or pressure on the soil specimen 48, on the other hand for allowing the air or water-vapor from the relative humidity control system 16 get passage through the soil specimen 48. Meanwhile due to the provision of these two porous disks 72 and 74, the soil-water contained in the soil specimen 48 will be forced out of the soil specimen 48 during extraction and enter into the relative humidity control system 16.

The second main part of the pressure plate extractor 10 of this invention is the use of a differential pressure detector 14, which is connected to the inner chamber 56 and the reference tube 62 through a tube 76 and 78, respectively. To minimize the potential expansion/compression of the connecting tubes 76 and 78 due to application of cell pressure, bronze tubes are used. The water level 64 in the reference tube 62 and the water level 60 in the inner cell 20 are detected, and the difference of these two water levels 60 and 64 is measured by the differential pressure detector 14. In this invention, a high-accuracy differential pressure transducer is used as the differential pressure detector 14. In particular, a model of Druck LPM9381 differential pressure transducer (DPT) is adapted.

The third main part of the pressure plate extractor 10 of this invention is the use of a relative humidity control system 16. The relative humidity control system 16 includes an electronic balance 82 and a desiccator 84 sit on balance 82. An aqueous solution 86 is stored in the desiccator 84. The aqueous solution 86 is made of sodium chloride solution. The relative humidity is controlled by adjusting the salt concentration of the aqueous solution 86. It is understood that the other solution could be used for adjusting and controlling the relative humidity. It is also understood that the other relative humidity regulator could be adapted for this purpose.

Through a tube, the desiccator 84 is connected with the porous disk 74 which is used to support the soil specimen 48.

The adjusted and controlled air or water-vapor is pumped into the soil specimen 48 through the tube by a conventional air pump 90 installed on the tube. Through another tube, the desiccator 84 is connected with the porous disk 72 which is used to cover the soil specimen 48. There is a flow meter 98 which is installed on the tube for monitoring the air or water-vapor flow rate. Therefore, the air or water-vapor under a controlled relative humidity will circulate between the soil specimen 48 and the relative humidity control system 16.

In order to measure and control the relative humidity of the soil specimen 48 more accurately, a set of relative humidity sensors 44 is installed at the center portion of each porous disk. A set of thermocouple psychrometers 94 is also installed at the center portion of the porous disk 72 and 74. The thermocouple psychrometer 94 is used for measuring the total suction.

In order to give a better understanding of how to operate the new pressure plate extractor 10, the practical operation aspects of this invention will be demonstrated as below.

Net stress control: The double-cell pressure plate extractor 10 according to this invention could be used for various purposes of net stress control.

First of all, like the conventional designs of pressure plate extractor, the new double-cell extractor 10 can control the net stress one-dimensionally by applying axial force only on the specimen 48.

The soil specimen 48 is covered by two porous disks 72 and 74, and then sealed within an impermeable membrane in the radial direction of the soil specimen 48. Then the soil specimen 48 is placed inside the inner cell 20. The extractor 10 is sealed to ensure air tightness of the whole system. De-aired water is used inside the extraction device 12.

During the process of extraction, an axial force is applied on the specimen 48 by the vertical loading system 30, and at the same time no pressurized air is introduced into the extraction device 12. The internal load cell 34 is attached to the loading arm 32 for measuring the axial force applied on the soil specimen 48 directly. The dial gauge 96 is mounted on the loading arm 32 for measuring the axial displacement of the soil specimen 48 during extraction. Therefore, the one-dimensional stress state is obtained in a controllable way.

Secondly, the new double-cell extractor 10 can control the net stress three-dimensionally by applying cell pressure only on the specimen 48. The cell pressure is applied to act on a soil specimen 48 isotropically ($\sigma=\sigma_1=\sigma_3$) via a pressurized air supply source through the port 66 on the top plate 22 into the outer cell 18 and inner cell 20, where $\sigma_1$ and $\sigma_3$ are major and minor principal stresses, respectively. The $\sigma_1$ (the major principal stress) stands for the stress in a vertical direction of the soil specimen 48, and the $\sigma_3$ (the minor principal stress) stands for the stress in a radial direction of the soil specimen 48.

Like the one-dimensional net stress control, the soil specimen 48 is sealed and placed inside the inner cell 20. The extractor 10 is sealed to ensure air tightness of the whole system. De-aired water is used inside the extraction device 12.

During the process of extraction, the pressurized air is introduced into the extraction device 12 via a pressurized air supply source through the port 66 on the top plate 22. The introduced pressurized air will control the pressure of the cell water 100, which in turn will pressurize the soil specimen 48 three-dimensionally, i.e. in both vertical direction and radial direction of the soil specimen 48. The vertical loading means 30 is not activated at the same time, and hence no axial force is applied on the specimen 48. Hence, a three-dimensional stress state is obtained, in which the stress in the vertical direction equals to that in the radial direction.

Thirdly, the new double-cell extractor 10 can control the net stress three-dimensionally by independently controlling both cell pressure and axial force on the specimen 48 simultaneously. So the SDSWCC test can be carried out under various deviatoric stress conditions ($\sigma_1 \neq \sigma_3$), wherein the $\sigma_1$ and $\sigma_3$ have the same meanings as mentioned above.

The axial force is exerted on a soil specimen 48 through the vertical loading system 30. The axial force applied on the soil specimen 48 is measured directly by the internal load cell 34 attached to the loading arm 32. The axial displacement of the soil specimen 48 is measured by the dial gauge 96 mounted on the loading arm 32.

Meanwhile, the cell pressure is applied on the soil specimen 48 by introducing pressurized air into the inner cell 20 and outer cell 18 from the port 66 on the top plate 22. As the inner cell 20 is an open-ended design, an identical pressure can be applied to both the inner cell 20 and the outer cell 18. The axial force applied by the vertical loading system 30 and cell pressure applied by the introduction of pressurized air are controlled independently and simultaneously. Therefore, by the combination of provision of the vertical loading system 30 and the introduction of the pressurized air supply, a three-dimensional stress is applied to the soil specimen 48 in a controllable way.

Finally, the total volume change of the soil specimen 48 under different stress states mentioned above is measured by a differential pressure detector 14.

Measurement of total volume changes of soil specimen: The total volume change of an unsaturated soil specimen 48 can be measured accurately throughout a SDSWCC test by application of the new pressure plate extractor 10 of this invention.

The basic principle of the measuring system is to record changes of differential pressure between a reference tube 62 and a bottle-shaped inner cell 20. Changes of the water level 60 inside the inner cell 20 resulted from any volume changes of the soil specimen 48 are compared with the constant water level 64 inside the reference tube 62, and measured by the accurate differential pressure detector 14. During a test, the change of water level 60 takes place only within the bottle neck of the inner cell 20. Thus, the measurement of the water level 60 inside the inner cell 20 due to any volume changes of the soil specimen 48 will become more sensitive because of the small cross-sectional area at the bottle neck. After that, the differential pressure change will be converted into volume change of the soil specimen 48, and finally the volume change of the soil specimen 48 resulted from various stress-states is obtained.

Meanwhile, the relative humidity of the soil specimen 48 and hence the total suctions can be controlled by a relative humidity control system 16 throughout the SDSWCC test by application of the new pressure plate extractor 10 of this invention.

Total suction control: In this application of the invention, the following thermodynamic equation proposed originally by Richards [Fredlund, D. G. and Rahardjo, H. (1993). *Soil mechanics for unsaturated soils*. John Wiley & Sons, Inc.] describing the relationship between total suction and relative humidity (RH) is employed for the control of total suction ($\psi$) applied to a soil specimen:

$$\psi = -\frac{RT}{v_{w0}\omega_v}\left[\ln\left(\frac{u_v}{u_{v0}}\right)\right] = -\frac{RT}{v_{w0}\omega_v}[\ln(RH)]$$

Where
R=universal molar gas constant (i.e. 8.31432 J/(mol K)),
T=absolute temperature,
$v_{w0}$=specific volume of water or the inverse of the density of water at given T,
$\omega_v$=molecular mass of water-vapor,
$u_v$=partial pressure of pore water-vapor,
$u_{v0}$=saturation pressure of water-vapor over a flat surface of pure water at the same temperature T.

It should be noted that the term ($u_v/u_{v0}$) is also called relative humidity (RH). Based on the above thermodynamic equation, it can be readily seen that total suction ($\psi$) in a soil specimen 48 can be controlled by applying different magnitudes of relative humidity (or partial vapor pressures) to the soil specimen 48, in this invention, by the use of the relative humidity control system 16. The magnitude of the relative humidity is regulated by adjusting the salt concentration of an aqueous solution 86 (i.e. saline solution) which is stored in a desiccator 84. An air pump 90 is used to drive air or water-vapor from the headspace of the desiccator 84 through the soil specimen 48, and a flow meter 94 is installed along the return line to monitor the air or water-vapor flow rate. The air or water-vapor from the relative humidity control system 16 enters into the soil specimen 48 and backflows into the desiccator 84. Hence, the air or water-vapor under controlled relative humidity circulates between the soil specimen 48 and the desiccator 84. Therefore, the relative humidity of the soil specimen 48 will become the same as the relative humidity of the air or water-vapor after being circulated for a period long enough. Then the relative humidity of the soil specimen 48 will be remained as the same as the relative humidity of the air or water-vapor during extraction.

At the top and the bottom of the soil specimen 48, two relative humidity sensors 44 are installed for measuring the actual relative humidity of the soil specimen 48. In addition, two thermocouple psychrometers 94, one at the top and the other one at the bottom of the soil specimen 48, are provided for measuring total suctions up to 8,000 kPa.

It should be noted that before conducting tests, calibrations are required to be carried out to account for apparent volume changes due to changes in cell pressure, fluctuations in the ambient temperature, creep of the inner cell 20 and any relative movement between the loading rod 36 and the inner cell 20. For example, the estimated accuracy of volume measurement is about 0.03% volumetric strain once the system is properly calibrated for a given soil specimen 48 of 70 mm in diameter and 19 mm in height.

It is understood that the various preferred version of the invention are shown and described above to illustrate different features of the invention and the ways in which these features may be obtained. However, this invention is not intended to be limited to the aforesaid embodiment, but rather is intended to be limited only by the claims below. Thus, this invention encompasses all different versions that fall literally or equivalently within the scope of the claims.

What is claimed is:

1. A pressure plate extractor for determining stress-dependent soil-water characteristic of a specimen, the pressure plate extractor comprising:
   a vessel having an outer wall,
   a vertical loading system located within the vessel for applying force on a specimen,
   a port in the outer wall for introducing a pressurized air supply into the vessel, and
   a relative humidity control system for controlling the humidity of the specimen by circulating fluid of a regulated humidity through the specimen.

2. The pressure plate extractor of claim 1, wherein the vessel has an inner wall defining a first and a second chambers within the vessel, the vertical loading system located within the first chamber, and the port introducing pressurized air supply into the second chamber.

3. The pressure plate extractor of claim 2, wherein the inner wall has an opening such that the pressurized air can pass from the second chamber into the first chamber.

4. The pressure plate extractor of claim 3, wherein the introduced air applies three-dimensional stress on the specimen.

5. The pressure plate extractor of claim 3, wherein the vertical loading system penetrates through both the vessel and the opening for applying an axial force on the specimen.

6. The pressure plate extractor of claim 1, wherein the port introduces the pressurized air into the vessel, the introduced air applying three-dimensional stress on the specimen cooperatively with the vertical loading system.

7. The pressure plate extractor of claim 1, wherein the vertical loading system further comprises an internal load cell for determining the axial force applied to the specimen.

8. The pressure plate extractor of claim 1, wherein the vertical loading system further comprises a dial gauge for measuring any axial displacement of the specimen.

9. The pressure plate extractor of claim 2, wherein the diameter of upper portion is smaller than that of the other portion of the first chamber.

10. The pressure plate extractor of claim 2, wherein the first chamber is bottle-shaped.

11. The pressure plate extractor of claim 2, wherein the pressure plate extractor further comprises a reference tube within the vessel.

12. The pressure plate extractor of claim 10, wherein the reference tube is mounted onto an external sidewall of the inner wall.

13. The pressure plate extractor of claim 11, wherein the pressure plate extractor further comprises a differential pressure detector connected with both the reference tube and the first chamber for measuring any volume changes of the specimen.

14. The pressure plate extractor of claim 1, wherein the pressure plate extractor further comprises a differential pressure detector.

15. The pressure plate extractor of claim 1, wherein the pressure plate extractor further comprises two porous disks which sandwich the specimen.

16. The pressure plate extractor of claim 15, wherein the relative humidity control system is connected with each of the porous disks.

17. The apparatus of claim 1 wherein the humidity control system comprises an aqueous solution stored inside a desiccator and is arranged for regulation the salt concentration of said aqueous solution so as to regulate the humidity of the air or water vapor circulated through the specimen.

18. The pressure plate extractor of claim 1, wherein the pressure plate extractor further comprises a membrane for wrapping the specimen on a radial direction of the specimen.

19. The pressure plate extractor of claim 18, wherein the membrane is both impermeable and resilient.

20. A method for measuring soil-water characteristic of a specimen, comprising steps of
   a) sealing the specimen within an impermeable membrane on a radial direction of the specimen;
   b) applying at least one of an axial force, and a cell pressure on the specimen for controlling a stress-state of the specimen three-dimensionally;

c) measuring any volume changes of the specimen resulted from application of the at least one of the axial force and the cell pressure;

d) controlling relative humidity of the specimen by circulating air or water-vapor from a relative humidity control system through the specimen so as to control the total suction of the specimen.

21. The method of claim 20 wherein a first side of the specimen is covered by a first porous disk and a second side of the specimen is covered by a second porous disk and wherein the relative humidity control system is arranged for circulating regulated humid air or water vapor between the first and second porous disks.

22. The method of claim 20 wherein the humidity of the air or water vapor circulated by the humidity control system is regulated by controlling the salt concentration of an aqueous solution stored inside a desiccator.

23. A pressure plate extractor for determining stress-dependent soil-water characteristics of a specimen, the pressure plate extractor comprising:

a vessel having an outer wall, a vertical loading system located within the vessel for applying force on a specimen, a port in the outer wall for introducing a pressurized air supply into the vessel, a humidity inlet for directing humid air or water vapor into the specimen, and a humidity outlet for directing humid air or water vapor that has circulated through the specimen out of the vessel.

* * * * *